(12) United States Patent
Desouhant-Massacret

(10) Patent No.: US 9,006,496 B2
(45) Date of Patent: *Apr. 14, 2015

(54) METHOD OF SEPARATING PHENOLIC COMPOUNDS IN SALIFIED FORM

(71) Applicant: Rhodia Operations, Aubervilliers (FR)

(72) Inventor: Magali Desouhant-Massacret, Caluire (FR)

(73) Assignee: Rhodia Operations, Aubervilliers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/099,311

(22) Filed: Dec. 6, 2013

(65) Prior Publication Data

US 2014/0094628 A1 Apr. 3, 2014

Related U.S. Application Data

(63) Continuation of application No. 12/992,838, filed as application No. PCT/EP2009/055934 on May 15, 2009, now abandoned.

(51) Int. Cl.
| | |
|---|---|
| *C07C 37/82* | (2006.01) |
| *C07C 41/34* | (2006.01) |
| *C07C 41/36* | (2006.01) |
| *C07C 43/23* | (2006.01) |

(52) U.S. Cl.
CPC ............... *C07C 41/34* (2013.01); *C07C 37/82* (2013.01); *C07C 41/36* (2013.01); *C07C 43/23* (2013.01)

(58) Field of Classification Search
CPC .......... C07C 37/82; C07C 43/23; C07C 41/36
USPC ................... 568/432, 758, 763, 727
See application file for complete search history.

(56) References Cited

U.S. PATENT DOCUMENTS

| | | | |
|---|---|---|---|
| 4,303,531 A | 12/1981 | Kawabata et al. | |
| 5,124,490 A * | 6/1992 | Cipullo | 568/758 |
| 6,359,172 B1 * | 3/2002 | Kessels | 562/475 |
| 6,753,441 B1 | 6/2004 | Jouve et al. | |
| 8,431,750 B2 | 4/2013 | Maliverney et al. | |
| 2012/0264982 A1 | 10/2012 | Desouhant-Massacret | |

FOREIGN PATENT DOCUMENTS

| | | |
|---|---|---|
| DE | 19900382 | 2/2000 |
| EP | 0987245 | 3/2000 |
| FR | 2132364 | 3/1972 |
| GB | 655555 | 7/1951 |
| GB | 1377243 | 12/1974 |
| WO | WO 9965853 | 12/1999 |
| WO | WO 2008148760 | 12/2008 |

OTHER PUBLICATIONS

International Search Report, International Application No. PCT/EP2009/055934, dated Jun. 29, 2009.
You, J. et al.—"Optimization of Vanillin Synthesis from Glyoxylic Acid" Journal of Food Science and Biotechnology(2005) vol. 24, No. 4; pp. 1673-1689 (11 pages)—English Translation included.

* cited by examiner

*Primary Examiner* — Sudhakar Katakam
*Assistant Examiner* — Pancham Bakshi
(74) *Attorney, Agent, or Firm* — Beatrice C. Ortego

(57) ABSTRACT

The subject of the present invention is a method for separating phenolic compounds in salified form from a reaction medium comprising them. The method of the invention for separating phenolic compounds in salified form from an aqueous reaction medium resulting from the reaction of a phenolic compound and of glyoxylic acid in the presence of a base leading to a reaction medium comprising at least the excess of initial phenolic compound in salified form and the various mandelic compounds in salified form resulting from the reaction, is characterized by the fact that said reaction medium is brought into contact with a basic anion-exchange resin that leads to the selective attachment of the initial phenolic compound to said resin and to the recovery of an aqueous stream comprising the mandelic compounds in salified form resulting from the reaction, and that the phenolic compound in salified form attached to the resin is separated by a resin regeneration treatment.

17 Claims, No Drawings

025
METHOD OF SEPARATING PHENOLIC COMPOUNDS IN SALIFIED FORM

CROSS-REFERENCE TO RELATED APPLICATIONS

This application is a Continuation of U.S. patent application Ser. No. 12/992,838, filed Jun. 9, 2011, which is the U.S. National Phase of International Application No. PCT/EP2009/055934 filed on May 15, 2009, which claims priority to French Application No. FR 08/02784 filed May 22, 2008, both of which are incorporated by reference herein in their entireties.

FIELD OF THE INVENTION

The present invention provides a method of separating phenolic compounds in salified form from a reaction mixture comprising them.

More specifically the invention relates to the separation of guaiacol or of guaethol in salified form from the synthesis mixtures comprising them.

The invention is directed more particularly to the recovery of guaiacol in the form of sodium salt, present in excess amount, during the synthesis of vanillin or 4-hydroxy-3-methoxybenzaldehyde.

BACKGROUND OF THE INVENTION

Hydroxyaromatic and alkoxyaromatic aldehydes are very important products, which are used as flavors and fragrances and as intermediates in numerous fields, such as, for example, agrochemicals, pharmacy, cosmetology, and other industries.

The ortho- and para-hydroxybenzaldehydes, 4-hydroxy-3-methoxybenzaldehyde and 3-ethoxy-4-hydroxybenzaldehyde, named "vanillin" and "ethylvanillin" respectively, are among the most important products.

Various processes have been proposed for the synthesis of aromatic aldehydes.

The most important processes are based on the functionalization of a phenolic starting compound, phenol, catechol derivative, guaiacol (or 2-methoxyphenol), guaethol (or 2-ethoxyphenol).

In this type of process, the phenolic compound is generally involved in a salified form, for example, in the form of a sodium salt.

Thus, for example, numerous processes for preparing vanillin involve a guaiacol salt as substrate, to which is then added a formyl group, in the position para to the hydroxyl group, by various methods.

One conventional route to vanillin involves a condensation reaction of glyoxylic acid with guaiacol, in basic medium, to give 4-hydroxy-3-methoxymandelic acid. This product is then oxidized to produce vanillin.

The reaction is commonly conducted in the presence of sodium hydroxide and with an excess of guaiacol, with glyoxylic acid being the deficit reactant.

Thus, at the end of the condensation reaction, an aqueous reaction mixture is obtained that comprises the sodium salt of 4-hydroxy-3-methoxymandelic acid, the precursor to vanillin, secondary products, such as the sodium salts of 2-hydroxy-3-methoxymandelic acid and 4-hydroxy-5-methoxy-1,3-dimandelic acid, and a greater or lesser excess of sodium guaiacolate.

In this reaction mixture, therefore, there are a number of types of salified phenolic compounds present, namely guaiacol in excess in the form of sodium guaiacolate, and the products of the reaction which are also salified phenolic compounds, such as the sodium salts of 4-hydroxy-3-methoxymandelic acid, 2-hydroxy-3-methoxymandelic acid, and 4-hydroxy-5-methoxy-1,3-dimandelic acid.

For economic reasons it is important to recover the unreacted starting substrate. However, the operation is not easy, since the guaiacol is in the form of sodium guaiacolate and is present alongside phenolic compounds which are also salified and have a closely related structure.

In certain processes described in the prior art, especially in FR 2 132 364, the sodium guaiacolate, at the end of the condensation reaction, is converted to guaiacol by an acid treatment, most often with sulfuric acid.

The unconverted guaiacol is then extracted from the acid solution by an extraction treatment using a hydrocarbon, for example, benzene or toluene.

The drawback of a method of this kind is that it employs an organic solvent, thereby giving rise to additional distillation operations in order to be able to recycle the organic solvent and the substrate recovered. Moreover, in the course of the distillation, there are secondary reactions which lead to the formation of heavy products.

Furthermore, the neutralization of sodium guaiacolate with sulfuric acid produces sodium sulfate, leading to the formation of substantial salt effluents.

Moreover, the guaiacol recovered must be salified again in order to be introduced into the condensation reaction with glyoxylic acid.

Similarly, the reaction mixture, comprising the mandelic compounds with a free hydroxyl group, must be salified again in order to be introduced into the oxidation reaction that allows vanillin to be obtained.

In order to overcome these drawbacks, the invention provides a method that allows the excess of phenolic starting compound in salified form, especially sodium guaiacolate, to be recovered, by a method which does not involve this step of neutralizing sodium guaiacolate to guaiacol, with the attendant need for said guaiacol to be extracted using an organic solvent which must subsequently be separated by distillation.

SUMMARY OF THE INVENTION

A method has now been found, and constitutes the subject of the present invention, of separating phenolic compounds in salified form from an aqueous reaction mixture resulting from the reaction of a phenolic compound and glyoxylic acid in the presence of a base, leading to a reaction mixture comprising at least the excess of phenolic starting compound in salified form and the various mandelic compounds in salified form, resulting from the reaction, characterized in that said reaction mixture is contacted with a basic anion-exchange resin, leading to the selective attachment of the phenolic starting compound to said resin, and to the recovery of an aqueous stream comprising the mandelic compounds in salified form obtained from the reaction, and in that the phenolic compound in salified form that is attached to the resin is separated by a regenerative treatment of the resin.

DETAILED DESCRIPTION OF THE INVENTION

In the description below of the present invention, the term "phenolic starting compound" means a benzene compound in which at least one hydrogen atom directly bonded to the benzene nucleus is substituted by a hydroxyl group.

In accordance with the method of the invention, it has been found, in the case of the treatment of an aqueous reaction mixture comprising sodium guaiacolate, that the latter can be attached to the resin in a salified form, thereby allowing it to be subsequently recycled to the synthesis step without the need to pass via a step of acidification of the sodium guaiacolate in order to convert it to guaiacol, which is recovered and then subjected to a further basic treatment, since the compound employed in the condensation step is a phenolate.

In order to illustrate the method of the invention, the Applicant is citing the case of the separation of sodium guaiacolate from the aqueous mixture from condensation of sodium guaiacolate and glyoxylic acid.

However, the method of the invention is not limited to the separation of this substrate, and is also suitable for phenolic starting compounds in salified form corresponding to the following formula:

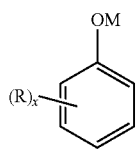

(I)

in which formula:
R is an alkyl or alkoxy group having from 1 to 4 carbon atoms, or a halogen atom,
x is a number from 0 to 3, and more preferably is 1, and
M represents a cation of a metallic element from group (IA) of the periodic table, namely lithium, sodium, potassium, rubidium, and cesium, or an ammonium cation.

In the formula (I), M is preferably sodium.

Examples of alkyl groups include linear or branched alkyl groups having from 1 to 4 Carbon atoms, such as methyl, ethyl, n-propyl, isopropyl, n-butyl, isobutyl, sec-butyl, and tert-butyl. Among these, the methyl and ethyl groups are preferred.

Examples of linear or branched alkoxy groups having from 1 to 4 carbon atoms include methoxy, ethoxy, n-propoxy, isopropoxy, n-butoxy, isobutoxy, and sec-butoxy groups. Methoxy and ethoxy groups are preferred.

R also represents a halogen atom, preferably fluorine, chlorine, and bromine, and more preferably fluorine.

With regard to the nature of R, it should be noted that the list of substituents given is not limitative, and other substituents may be envisaged insofar as they do not disrupt the separation of the compound of formula (I).

Illustrative instances of compounds corresponding to the formula (I) include, more particularly, the salts of compounds selected from the group consisting of the following: phenol, guaiacol, 3-methoxyphenol, guaethol, 3-ethoxyphenol, 2-isopropoxyphenol, 3-isopropoxyphenol, 2-methoxy-5-methylphenol, 2-methoxy-6-methylphenol, 2-methoxy-6-tert-butylphenol, 3-chloro-5-methoxyphenol, 2,3-dimethoxy-5-methylphenol, 2,3-dimethoxyphenol, 2,6-dimethoxyphenol, 3,5-dimethoxyphenol, cresols, tert-butylphenol, 2-methoxyphenol, and 4-methoxyphenol.

The preferred compounds of formula (I) are phenol, guaiacol, and guaethol.

According to the invention, the method of the invention is applied to the aqueous reaction mixture obtained from the reaction of a phenolic compound in salified form of formula (I) and glyoxylic acid.

The condensation reaction of the phenolic compound of formula (I) and glyoxylic acid may be conducted in the presence of an ammonium hydroxide, but more preferably in the presence of an alkali metal hydroxide, which may be sodium hydroxide or potassium hydroxide. For economic reasons it is preferred to select sodium hydroxide.

With regard to the glyoxylic acid, an aqueous solution of glyoxylic acid is employed that has a concentration of, for example, between 15% and 70% by weight.

The glyoxylic acid is reacted with the phenolic compound of formula (I) in excess. The molar ratio between the phenolic compound of formula (I) and the glyoxylic acid is between 1.1 and 4.0, preferably between 1.5 and 3.0.

The alkali metal hydroxide solution employed has a concentration of generally between 10% and 50% by weight.

The amount of alkali metal hydroxide introduced into the reaction mixture takes account of the amount needed in order to salify the hydroxyl function of the phenolic compound of formula (I), and the amount needed to salify the carboxyl function of the glyoxylic acid.

The concentration of the phenolic compound of formula (I) is preferably between 0.5 and 1.5 mols/liter.

The temperature of the reaction is selected advantageously between 20° C. and 60° C.

The reaction is conducted at atmospheric pressure but under a controlled atmosphere of inert gases, preferably nitrogen or rare gases, especially argon. It is preferred to select nitrogen.

After the phenolic compound of formula (I) has been contacted with the glyoxylic acid and the alkali metal hydroxide, the reaction mixture is maintained with stirring and at the temperature selected from the aforementioned range, for a variable duration of from 1 to 10 hours.

At the end of the reaction, an aqueous reaction mixture is obtained that comprises the excess of phenolic compound in salified form corresponding to the formula (I) and various mandelic compounds in salified form, denoted by the expression "mandelic compounds" and corresponding to the following formulae:

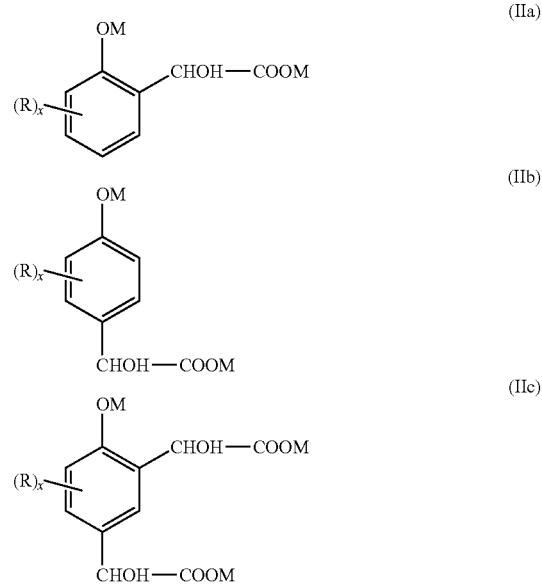

in which formulae M, R, and x are as defined for the formula (I).

The preferred mandelic compounds correspond to the formulae (IIa), (IIb) and (IIc), in which M represents a sodium atom, x is a number from 0 to 3, and preferably is 1, and the groups R, which are identical or different, represent an alkyl or alkoxy group having from 1 to 4 carbon atoms, preferably a methoxy or ethoxy group, or a halogen atom.

The invention applies more particularly, in the context of the preparation of vanillin, to an aqueous mixture comprising sodium guaiacolate and mandelic compounds in salified form: 4-hydroxy-3-methoxymandelic acid, 2-hydroxy-3-methoxymandelic acid, 4-hydroxy-5-methoxy-1,3-dimandelic acid, in salified form.

The invention is also applied preferably, for the preparation of ethylvanillin, to a reaction mixture which is an aqueous mixture comprising sodium guaetholate and mandelic compounds in salified form: 3-ethoxy-4-hydroxymandelic acid, 3-ethoxy-2-hydroxymandelic acid, 5-ethoxy-4-hydroxy-1,3-dimandelic acid, in salified form.

The concentration by weight of the phenolic starting compound in salified form, preferably sodium guaiacolate or sodium guaetholate, varies generally between 1% and 20% by weight, preferably between 5% and 10% by weight.

The concentration by weight of mandelic compounds (o-, p-, and di-mandelate) in the reaction mixture is typically between 3% and 30% by weight, preferably between 5% and 20% by weight.

The method of the invention for separating the phenolic compound in salified form is therefore implemented on the aqueous reaction mixture as defined above.

In the case of the preparation of vanillin and of ethylvanillin, the mixture therefore comprises sodium guaiacolate or sodium guaetholate and various reaction products, namely monofunctional or difunctional sodium mandelates as specified in accordance with formulae (IIa), (IIb), and (IIc), predominantly the compound of formula (IIb).

In accordance with the method of the invention, the reaction mixture as described above is contacted with a basic resin, leading to the attachment to the resin of the phenolic compound in salified form, and to the recovery of an aqueous stream comprising the products of the reaction.

The reaction mixture to be treated is therefore contacted with a basic, preferably weakly basic, anion-exchange resin.

The resins are polymeric structures which carry functional groups such as primary, secondary or tertiary amino or quaternary ammonium groups.

Accordingly, the resins may comprise one or more functional groups corresponding to the following formulae:

   (F₁)

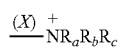   (F₂)

in which formulae:
    the groups $R_a$, $R_b$, and $R_c$, which are identical or different, represent a $C_1$-$C_4$-alkyl group, preferably methyl or ethyl, a phenyl group, a benzyl group, or a hydroxyalkyl group, preferably a β-hydroxyethyl group,
    not more than two of the groups $R_a$, $R_b$ and $R_c$ are hydrogen atoms, and
    (x) symbolizes the bond connecting the nitrogen atom to the polymeric structure.

One very preferred group of resins very suitable for the method of the invention is composed of resins formed from a polystyrene backbone which carries basic functional groups as defined above.

The polystyrene backbone is obtained by polymerizing styrene and divinylbenzene, under the influence of an activation catalyst, usually an organic peroxide, leading to a crosslinked polystyrene. The polymerization takes place usually in suspension, and produces beads or granules of polymer. Generally, these beads of crosslinked polystyrene are functionalized by treating them with chloromethyl ether in an anhydrous medium and in the presence of a catalyst (for example, $AlCl_3$ or $SnCl_4$), and then the chloromethylated polystyrene obtained, denoted as functionalized polymer P, is reacted with an amine or with ammonia, thereby allowing the chlorine of the chloromethyl group to be replaced by the basic functional group.

The amine is advantageously a secondary or tertiary amine, and corresponds to the following formula:

$$NR_aR_bR_c \quad (III)$$

in which formula:
    the groups $R_a$, $R_b$, and $R_c$, which are identical or different, represent a $C_1$-$C_4$-alkyl group, preferably methyl or ethyl, a phenyl group, a benzyl group, or a hydroxyalkyl group, preferably a β-hydroxyethyl group,
    not more than two of the groups $R_a$, $R_b$, and $R_c$ are hydrogen atoms.

Therefore, in the method of the invention, it is advantageous to select a weakly basic resin.

Resins considered weakly basic include resins which carry secondary amino (type —$NHR_a$) or tertiary amino (type —$NR_aR_b$) functions.

They are obtained, respectively, by reacting the functionalized polymer P with a primary amine $R_a$—$NH_2$ or with a secondary amine $R_aR_bNH$. Methylamine and dimethylamine are examples of such amines.

The commonest weakly basic resins are those which carry tertiary amine functions.

When the functionalized polymer P is reacted with a tertiary amine, the resulting resin carries a quaternary ammonium function —$N^+R_aR_bR_c$, which gives it a strongly basic character.

The resins having a polystyrene backbone are employed preferably in the method of the invention. However, the invention does not rule out the use of resins having a backbone of some other kind, with the proviso that the backbone carries the appropriate basic groups.

Likewise suitable for the method of the invention, therefore, are polyacrylic resins.

Their preparation is similar to that of the polystyrene resins.

Beads are prepared from an acrylic ester and divinylbenzene, which are copolymerized in suspension in the presence of a free-radical activation catalyst. The acrylic polyester thus formed is reacted with a polyamine containing at least one primary amine function and one secondary or tertiary amine function. The primary amine function reacts with the ester function of the polymer, leading to an amide function, while the other amino-functional group as defined constitutes the active anion-exchange group.

Numerous resins are commercially available products in dry or wet form. One or other of the forms may be used in the method of the invention.

The resins in question may be gel resins or macroporous resins; the latter type of resins is preferred.

The resins are typically present in the form of substantially spherical particles having a diameter of from 0.3 to 1.5 mm, preferably between 0.3 and 1.2 mm.

The concentration of (basic) active sites on the resin is advantageously between 1 and 3 milliequivalents of active sites per liter of dry polymer, and, preferably, between 1.2 and 1.8 milliequivalents of active sites per liter of dry polymer.

On the market there are resins which are commercialized under various trade names. These include, among others, the following resins: Amberlite IRA96RF, Amberlite IRA 67, Amberlyst® A21, Amberlyst® A23, and Amberlyst® A24; sold by Rohm & Haas; Lewatit MonoPlus® MP64, Lewatit MP 62, Lewatit VP OC 1072, Lewatit MonoPlus® MP64, Lewatit MP 62 WS, Lewatit S 4268, Lewatit S 4228, Lewatit S 4328, Lewatit S 4428, and Lewatit S 4528, sold by Lanxess; WBG30, WBG30-B, WBMP, and WBACR, sold by Resin-Tech; Dowex 22, Dowex 66, Dow-ex Monosphere 66, Dowex Monosphere 77, Dowex Marathon WBA, Dowex Marathon WBA-2, Dowex UPCORE Mono WB-500, Dowex M-43, and XUS 43568.00 sold by Dow Chemical Co.; Purolite A100 and A847 from Purolite Co.; and XA 3031, XA 3032, XA 3041, XA 3042, XA 3043, XA 3051, XA 3053, XA 3061, XA 3062, XA 3111, XA 3112, and XA 3251, which are sold by Novasep.

Amberjet 4400 and Amberlyst A26 and Dowex 22 are examples of strong basic resins which may be suitable.

Among the aforementioned resins, the preferred resins are the weakly basic resins, such as, more particularly, the following: Amberlyst A21, Amberlite IRA 67, Lewatit MP 64, Lewatit MP 62, and Purolite A100.

In accordance with the method of the invention, the reaction mixture obtained at the end of the condensation reaction is passed over the anion-exchange resin.

The stream is thus at a temperature close to the condensation temperature of between 20° C. and 60° C.

Generally speaking, the resin is placed in a stirred reactor or else in a column, the medium being introduced generally from top to bottom.

The amount of resin employed is at least equal to the amount of phenolic compound in salified form that is to be recovered.

At the column bottom an aqueous stream is recovered that comprises all of the mandelic compounds in salified form, while the phenolic compound in salified form, preferably sodium guaiacolate or sodium guaetholate, is attached to the resin.

The aqueous stream comprising the mandelic compounds in salified form may be directly input into the oxidizing operation, thereby making it possible to obtain the aromatic aldehyde corresponding to the mandelic compounds in salified form.

In a subsequent step, the phenolic compound in salified form is recovered by regeneration of the resin.

Regeneration of the resin by means of a base is selected with preference.

Suitable bases include, in particular, sodium hydroxide, aqueous ammonia, and sodium carbonate.

For this purpose, a basic treatment is carried out, preferably using a basic aqueous solution, having a concentration of 2% to 10% by weight, and more preferably between 3% and 8% by weight. Sodium hydroxide is typically used.

The amount of base employed is at least equal to the amount of phenolic compound in salified form that is to be regenerated.

A solution is thus obtained of the phenolic compound, which is salified and can therefore be recycled directly to the condensation step.

As mentioned above, the method of the invention makes it possible to separate an aqueous stream comprising the various mandelic compounds in salified form.

Accordingly, the method of the invention allows access to hydroxyaromatic aldehydes corresponding to the formulae (IIa), (III)), and (IIc) in which the glycol group of formula —CHOH—COOH is replaced by a formyl group CHO.

The oxidation reaction may be conducted according to the techniques that are described in the literature. Thus it is possible to use the catalysts that are conventionally used in oxidation reactions of mandelic compounds in a basic medium.

The oxidation is generally conducted by oxygen or air under pressure, in the presence of an appropriate catalyst such as, for example, derivatives of chromium, manganese, iron, cobalt, nickel, copper, zinc, bismuth, aluminum, silver, vanadium or osmium.

It should be noted that this list is not limitative.

It is possible, very particularly, to employ oxides, sulfates, halides, and acetates of said metallic elements.

It is also possible to use a catalyst comprising at least two metallic elements. Reference may be made more particularly to WO 2008/148760, which proposes the use of a catalyst system comprising at least two metallic elements, $M_1$ and $M_2$, which are selected from the group consisting of copper, nickel, cobalt, iron, and manganese.

Accordingly, the invention allows easy access to hydroxybenzaldehydes, and more particularly to vanillin and its analogs, for example, 3-ethylvanillin and 3-isopropylvanillin, by oxidation, respectively, of p-hydroxymandelic acid and of 4-hydroxy-3-methoxymandelic acid, 3-ethoxy-4-hydroxymandelic acid, or 4-hydroxy-3-isopropoxymandelic acid.

Working examples of the invention are given below by way of illustration and without any limitative character.

In the examples, the selectivity of the reaction is defined as the following ratio: [guaiacol]attached/([guaiacol]attached+ [mandelate]attached).

Example 1

In this example, the resin used is an Amberlyst A21 resin, which is a weakly basic anion-exchange resin functionalized with tertiary amines.

It takes the form of beads having an average diameter of between 0.490 and 0.690 mm. The average diameter is defined as being such that 50% by weight of the beads have a diameter greater than or less than the average diameter.

Its total exchange capacity is 1.3 min·eq/l.

Its BET specific surface area is 35 m²/g, the average diameter of the pores is 110 Å, and the total pore volume is 0.10 cm³/g.

A Schott tube is charged with 36.70 g of a stream comprising 2.14 g of sodium guaiacolate (0.014 mol) and 2.54 g of sodium p-mandelate (0.013 mol) of formula:

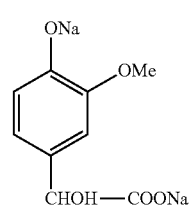

Then 4.2 g of Amberlyst 21 resin and 10.10 g of water are added.

Anion exchange is then followed by high-performance liquid chromatography analysis of said solution.

When resin is added to the stream, 30% of guaiacolate is attached.

After 35 minutes, 45% of guaiacolate is attached, with no attachment of mandelates.

The ratio defining the selectivity is 1.

Example 2

In this example, Lewatit MP64 resin is employed, which is a weakly basic anion-exchange resin based on a styrene-divinylbenzene copolymer having a macroporous structure and containing tertiary/quaternary ammonium functional groups.

It takes the form of beads with a uniform (monodisperse) diameter; 90% of the volume of the beads have a diameter of between 0.54 and 0.64 mm.

Its total exchange capacity is 1.3 min·eq/l.

Example 1 is repeated, with the only difference that the nature of the resin is changed.

With this resin, the selectivity obtained is 1.

Example 3

In this example, Amberlite IRA 67 resin is employed, which is a weakly basic anion-exchange resin having an acrylic gel matrix functionalized with tertiary amines.

Its total exchange capacity is 1.6 min·eq/l.

Example 1 is repeated, with the only difference that the nature of the resin is changed.

With this resin, the selectivity obtained is 1.

Example 4

In this example, the resin employed is Purolite A100, which is a weakly basic anion-exchange resin having a polystyrene matrix functionalized with tertiary amines.

The resin takes the form of beads with an average diameter of between 0.6 and 0.85 mm.

It total exchange capacity is 1.3 min·eq/l.

The resin is employed in a 300 ml column with a diameter of 2.8 cm and a height of 24 cm.

The volume of the resin is 150 ml.

The column is maintained under atmospheric pressure at 35° C.

This resin is percolated at a rate of 1.5 m/h with a stream comprising 5.2% of sodium guaiacolate and 5.9% of mandelic compounds in sodium salt form (o-, p-, and di-mandelate), obtained from a condensation reaction between glyoxylic acid and guaiacol, in the presence of sodium hydroxide, conducted according to the teaching of the prior art (WO 99/65853), and corresponding to the formulae (IIa), (IIb) and (IIc) in which R represents a methoxy group, x is 1, and M is sodium.

In this example, 380 g of the stream as defined above is percolated through the resin.

At the outlet from the column, 380 g of a stream which is free from sodium guaiacolate and contains all of the mandelic compounds in sodium salt form that were charged is recovered.

The ratio which defines the selectivity is 1.

The sodium guaiacolate attached to the resin is recovered by treatment with sodium hydroxide.

A 5% by weight aqueous solution of sodium hydroxide is percolated through the resin at a rate of 2 m/s.

A stream is recovered which contains sodium guaiacolate with a yield of 88% by weight, the yield being defined as the weight ratio (in %) between the guaiacolate introduced and the guaiacolate recovered.

This guaiacolate may be directly recycled to the condensation step.

The stream at the column outlet that contains the mandelic compounds in salified form is then oxidized without further addition of aqueous sodium hydroxide solution.

The stream is charged to a 316L stainless-steel reactor equipped with mechanical stirring, baffles, and an air inlet.

This reaction mixture is admixed with a catalyst system comprising $CoCl_2 \cdot 6H_2O$ and $CuSO_4 \cdot 5H_2O$, which are employed, respectively, in an amount, expressed as molar percentage of mandelic compounds, of 0.125 and 0.125.

The mixture is subsequently heated to 80° C. and air is introduced at a rate of 1.6 L/h.

After 30 minutes of reaction, a selectivity of the reaction for vanillin of 98% is obtained.

Example 5

Example 4 is reproduced, with the sole difference that the reaction mixture percolated results from the reaction of guaethol and glyoxylic acid in the presence of sodium hydroxide, and therefore comprises sodium guaetholate and the mandelic compounds in sodium salt form (o-, p-, and di-mandelate) which correspond to the formulae (IIa), (IIb), and (IIc) in which R represents an ethoxy group, x is 1, and M is sodium.

At the outlet from the column, a stream is recovered which is free from sodium guaetholate and contains all of the mandelic compounds in sodium salt form that were charged.

With this resin, the ratio which defines the selectivity is 1.

The invention claimed is:

1. A method of separating a phenolic compound in salified form from an aqueous reaction mixture resulting from a reaction of a phenolic compound and glyoxylic acid in the presence of a base,
   wherein the reaction mixture comprises excess phenolic compound in salified form and at least one mandelic compound in salified form, and
   said phenolic compound in salified form is a compound of formula (I),

(I)

wherein:
   R is an alkyl or alkoxy group having from 1 to 4 carbon atoms, or a halogen atom;
   x is an integer from 0 to 3; and
   M is a group (IA) alkali metal cation or an ammonium cation;
said method comprising:
   contacting said reaction mixture with a basic anion-exchange resin,
      wherein the phenolic compound in salified form selectively attaches to said resin,
   recovering an aqueous stream comprising the at least one mandelic compound in salified form, and
   separating the phenolic compound in salified form that is attached to the resin by a regenerative treatment of the resin which comprises treatment with a base.

2. The method of claim 1, wherein the phenolic compound in salified form comprises sodium guaiacolate, sodium guaetholate, or a mixture thereof.

3. The method of claim 1, wherein the reaction mixture comprises the excess phenolic compound in salified form at a concentration ranging from 1% to 20% by weight.

4. The method of claim 1 wherein the reaction mixture comprises products obtainable from the reaction of the phenolic compound of formula (I) and glyoxylic acid, in the presence of a base, wherein said at least one mandelic compound in salified form comprises at least one compound of formulae:

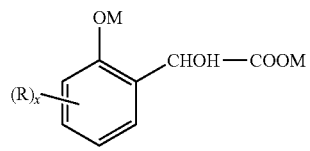

(IIa)

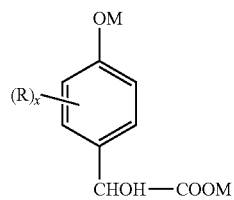

(IIb)

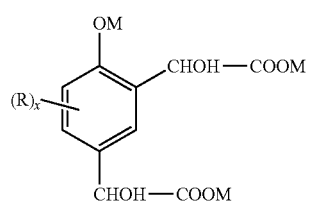

(IIc)

wherein:
R is an alkyl or alkoxy group having from 1 to 4 carbon atoms, or a halogen atom;
x is an integer from 0 to 3; and
M is a group (IA) alkali metal cation or an ammonium cation.

5. The method of claim 4, wherein M is a sodium atom.

6. The method of claim 1, wherein the reaction mixture comprises sodium guaiacolate and at least one mandelic compound in salified form comprising 4-hydroxy-3-methoxymandelic acid, 2-hydroxy-3-methoxymandelic acid, or 4-hydroxy-5-methoxy-1,3-dimandelic acid.

7. The method of claim 1, wherein the reaction mixture comprises sodium guaetholate and at least one mandelic compound in salified form comprising 3-ethoxy-4-hydroxymandelic acid, 3-ethoxy-2-hydroxymandelic acid, or 5-ethoxy-4-hydroxy-1,3-dimandelic acid.

8. The method of claim 1, wherein the reaction mixture comprises reaction products including mandelic acids in salified form at a concentration ranging from 3% to 30% by weight.

9. The method of claim 1, wherein the resin comprises a polymeric structure and includes a functional group comprising a primary, secondary or tertiary amino, a quaternary ammonium group, or a combination thereof.

10. The method of claim 9, wherein the resin comprises one or more functional groups comprising:

wherein:
the groups $R_a$, $R_b$, and $R_c$, which are identical or different, represent a $C_1$-$C_4$-alkyl group, a phenyl group, a benzyl group, a hydroxyalkyl group, or a hydrogen,
wherein not more than two of the groups $R_a$, $R_b$, and $R_c$ comprise a hydrogen atom, and
(x) symbolizes a bond connecting the nitrogen atom to the polymeric structure.

11. The method of claim 9, wherein the polymeric structure comprises a polystyrene or polyacrylic backbone.

12. The method of claim 9, wherein the resin comprises substantially spherical particles with diameters ranging from 0.3 to 1.5 mm.

13. The method of claim 9, wherein the resin comprises active sites in a concentration ranging from 1 to 3 milliequivalents of active sites per liter of dry polymer.

14. The method of claim 9, wherein the resin comprises a weakly basic resin.

15. The method of claim 9, wherein the resin comprises Amberlyst A21, Amberlite IRA 67, Lewatit MP 64, Lewatit MP 62, Purolite A100, or a mixture thereof.

16. The method of claim 1, further comprising recycling the separated phenolic compound to react with glyoxylic acid in the presence of a base.

17. The method of claim 1, further comprising oxidizing the at least one mandelic compound in salified form in the recovered aqueous stream to yield at least one aromatic aldehyde.

* * * * *